Figure 1:
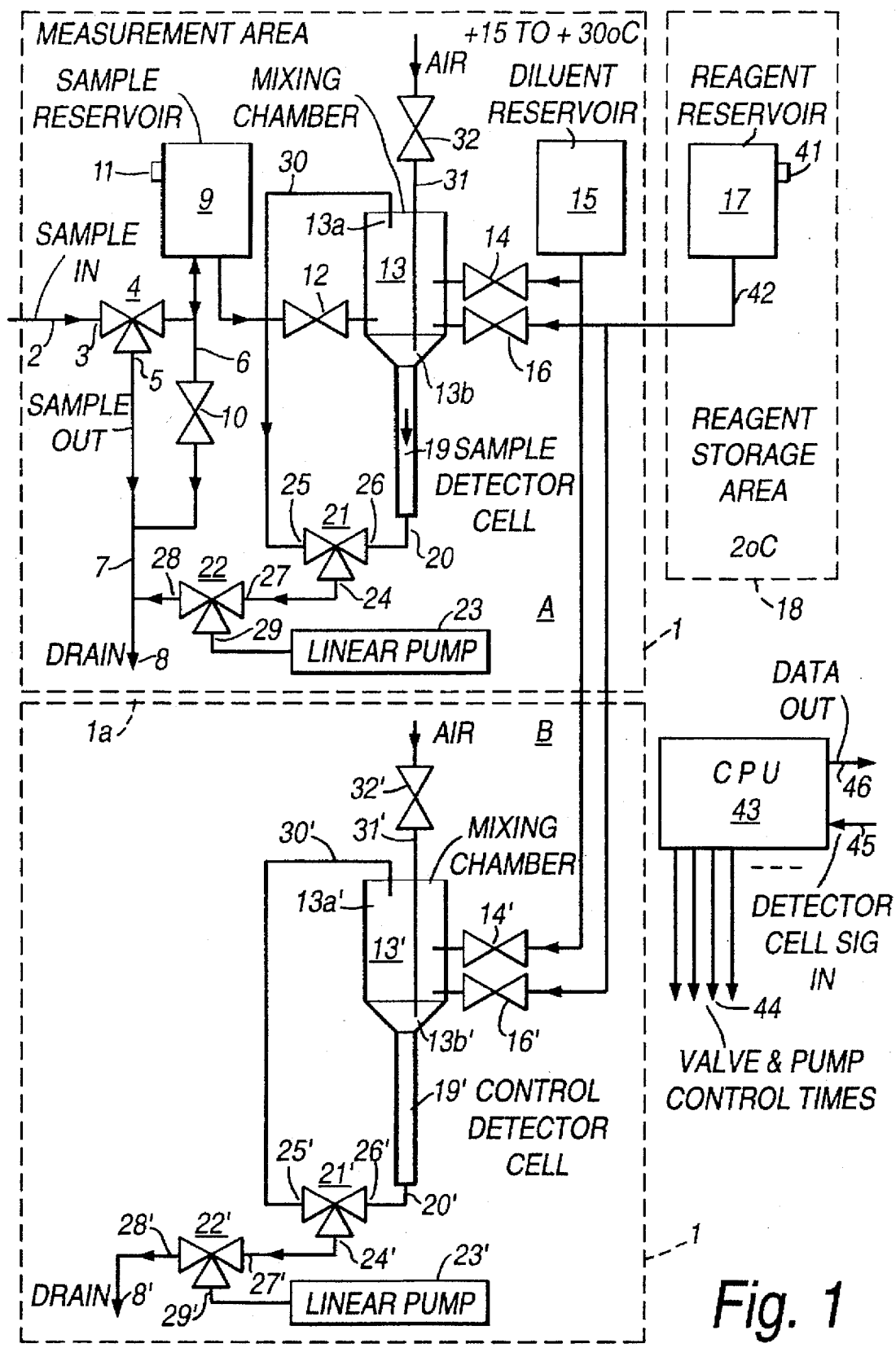

United States Patent [19]

Bartlett-Hooker et al.

[11] Patent Number: 5,668,330

[45] Date of Patent: Sep. 16, 1997

[54] AQUEOUS SAMPLE TESTING APPARATUS

[75] Inventors: William Bartlett-Hooker, Wimborne; Sanath Ediriweera, Poole; Stuart Ward, Bournemouth, all of England

[73] Assignees: Siemens, plc, Berkshire; Yorkshire Water plc, Leeds, both of England; Microbics Corp., Carlsbad, Calif.

[21] Appl. No.: 679,759

[22] Filed: Jul. 10, 1996

[30] Foreign Application Priority Data

Jul. 29, 1995 [GB] United Kingdom ............... 9515635

[51] Int. Cl.$^6$ ................................................. G01N 1/00
[52] U.S. Cl. ........................................ 73/864.81; 73/61.59
[58] Field of Search ........................... 73/61.59, 864.81; 422/81, 82.05, 82.08, 82.09; 356/36; 366/101, 106, 107

[56] References Cited

FOREIGN PATENT DOCUMENTS

| | | | |
|---|---|---|---|
| 996195 | 6/1965 | United Kingdom | 366/106 |
| WO95/00834 | 1/1995 | WIPO . | |

*Primary Examiner*—Robert Raevis
*Attorney, Agent, or Firm*—Keck, Mahin & Cate

[57] ABSTRACT

Toxicity measuring apparatus comprising a sample reservoir in which an aqueous sample to be tested is stored, a reagent reservoir, a diluent reservoir, a mixing chamber vented via a first valve to atmosphere through an air inlet tube which extends within the chamber towards a lower part thereof, second, third and fourth valves via which the sample, the reagent and the diluent respectively are fed selectively to the mixing chamber in accordance with the open/closed state of the said second, third or fourth valves, a toxicity detector cell fed with a mixture of the sample, the reagent and the diluent from the chamber, within which detector cell aqueous sample measurements are carried out, a linear pump and valve means, via which valve means the mixture is drawn through the detector cell from the chamber by the linear pump, or via which air in an upper part of the chamber is drawn from the chamber by the pump in accordance with the open/closed state of the said valve means, whereby for the purpose of mixing the sample, the reagent and the diluent, the said valve means is set so that air is drawn into the chamber via the inlet tube so as to bubble up through the mixture contained therein so as to effect mixing.

9 Claims, 3 Drawing Sheets

AQUEOUS SAMPLE TESTING APPARATUS

This invention relates to aqueous sample testing apparatus and more especially it relates to apparatus for measuring the toxicity of polluted water samples.

It is known to measure the toxicity of a polluted water based sample (i.e. an aqueous sample such as sewage, effluent, or any other water based sample) by mixing the sample to be tested with bacteria which naturally bioluminesces, the toxicity of the sample under test being indicated in dependence upon bioluminescence. A particularly suitable bacterium for toxicity measurement is the aquatic marine bacterium *Photobacterium phosphoreum*. The bioluminescence produced by the bacterium is a by-product of respiration. Toxins in the test sample which cause an inhibition of respiration, cause a reduction in the bioluminescence proportional to the level of toxicity present. Hence, a measurement of the bioluminescence may be used as an indication of toxicity.

Known toxicity measuring apparatus is manually operated, requiring the use of micro-burettes or similar devices to perform quantifiable dilutions of a test sample, or requiring the manual addition of a freeze-dried bacterial reagent to a fixed volume of sample. These operations all require a manual operator and some operations are prone to operator error (especially if dilutions are required). The freeze-dried bacterial reagent used is often stored remotely from the apparatus and is removed from cold storage only when required. The use of such apparatus for continuous monitoring of a sample stream is therefore labour intensive and tends to be prone to errors.

It is therefore an object of the present invention to provide apparatus for the toxicity measurement of aqueous samples which needs little manual attention and which provides substantially error free results.

According to the present invention, aqueous sample testing apparatus comprises a sample reservoir in which a sample to be tested is stored, a reagent reservoir, a diluent reservoir, a mixing chamber vented via a first valve to atmosphere through an air inlet tube which extends within the chamber towards a lower part thereof, second, third and fourth valves via which the sample, the reagent and the diluent respectively are fed selectively to the mixing chamber in accordance with the open/closed state of the said second, third or fourth valves, a detector cell fed with a mixture of the sample, the reagent and the diluent from the chamber, within which detector cell sample quality measurements are carried out, a linear pump and valve means, via which valve means the mixture is drawn through the detector cell from the chamber by the linear pump, or via which air in an upper part of the chamber is drawn from the chamber by the pump in accordance with the open/closed state of the said valve means, whereby for the purpose of mixing the sample, the reagent and the diluent, the said valve means is set so that air is drawn into the chamber via the inlet tube so as to bubble up through the mixture contained therein.

The term linear pump when used herein, is intended to mean a pump which sucks at a substantially constant rate, e.g. a piston pump, wherein for suction purposes, the piston is operated at a substantially constant linear velocity, each pumping operation being completed during one stroke of the pump.

The apparatus may include a central processor unit (CPU) used to control operation of the linear pump, the valves and the valve means in accordance with a predetermined programme.

It will be appreciated that by using a linear pump, i.e. a pump which provides substantially constant suction, the relative proportions of constituents of the mixture comprising the sample, the reagent and the diluent, may simply be controlled according to the period for which the valve via which a particular constituent of the mixture is fed to the mixing chamber, is opened.

It will also be appreciated that thorough mixing of the constituents of the mixture is simply achieved by bubbling air through the mixture in the mixing chamber.

The apparatus may be used for toxicity measurement of aqueous samples and accordingly the reagent may comprise bioluminescent bacteria in an aqueous solution, the diluent may comprise an aqueous solution, and the detector cell may comprise light detector means arranged for detecting light given off by the bioluminescent bacteria in the mixture present in the said cell.

The proportion of diluent to sample may be varied in dependence upon the toxicity of the sample as determined by the detector cell and for this purpose an appropriate signal may be transmitted from the cell to the computer.

Thus, the proportion of diluent to sample might be increased with toxicity of the sample.

The apparatus may comprise further valve means via which the sample in the sample reservoir may be replaced for further measurements.

In order to provide reference data appertaining to the sample which can be used to correct for errors produced due to colour or turbidity of the sample and to correct for natural changes in reagent bioluminescence, the diluent reservoir and the reagent reservoir may be coupled via additional valve means, to an additional mixing chamber, which additional mixing chamber is coupled to an additional detector cell, a toxicity measurement appertaining to the sample being produced in dependence upon data derived both from the said detector cell and the said additional detector cell.

The two detector cells may each comprise a light source operatively associated with a light detector positioned to receive light from the source after it has passed through the mixture in the cell with which it is associated and a bioluminescence detector for detecting light produced due to bacterial bioluminescence.

It will be appreciated that by taking into account the characteristics of the reagent and diluent alone, as measured in the additional detector cell, data derived in dependence upon these characteristics may be used for correction purposes, whereby accurate toxicity measurements are facilitated.

Figure 2A:
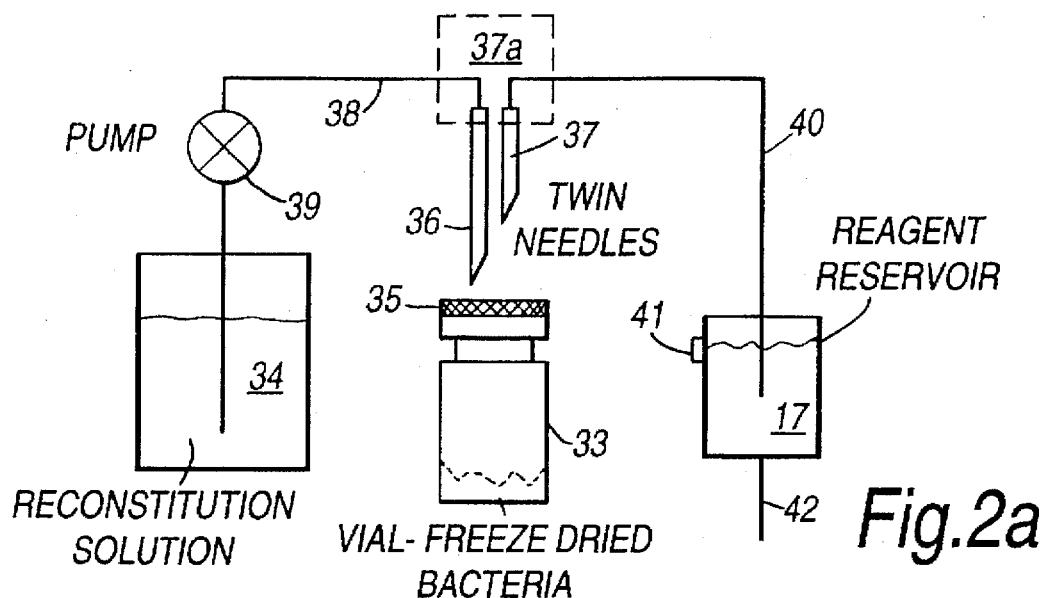
Figure 2B:
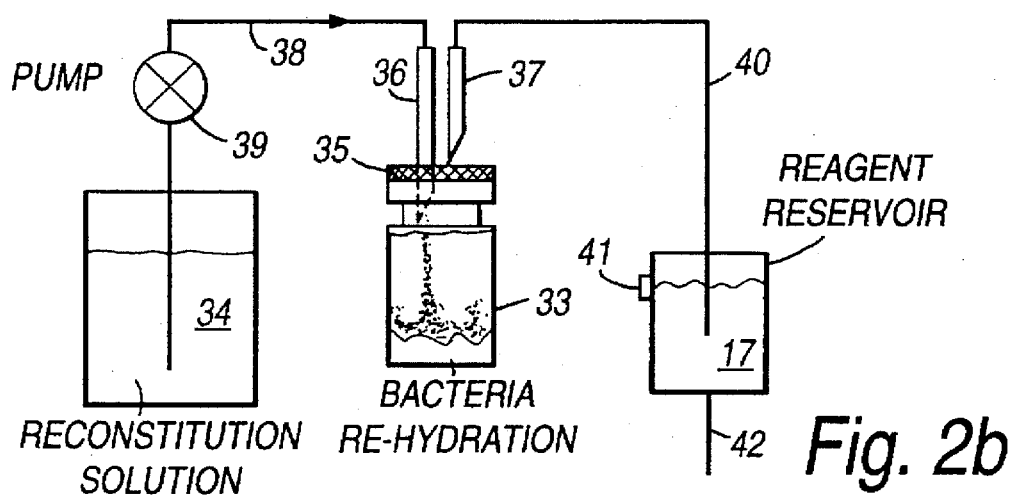
Figure 2C:
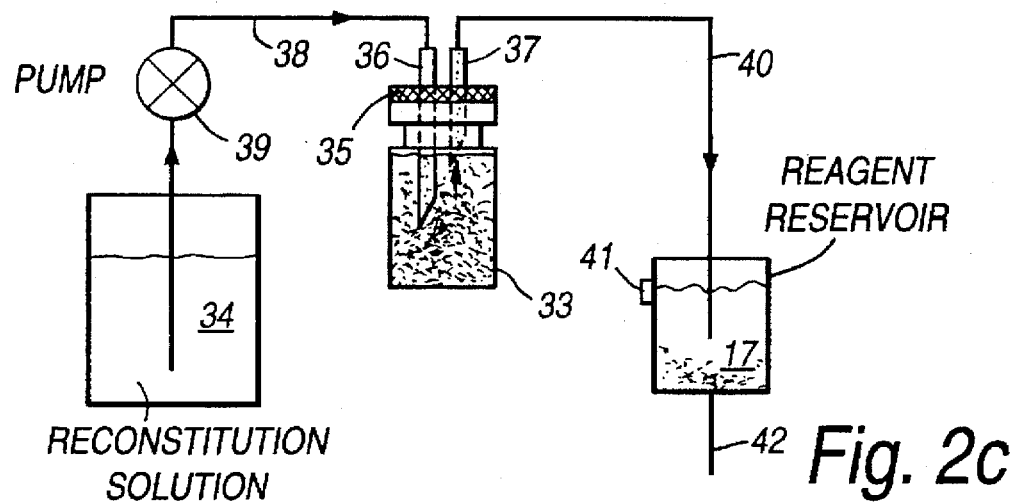
Figure 3A:
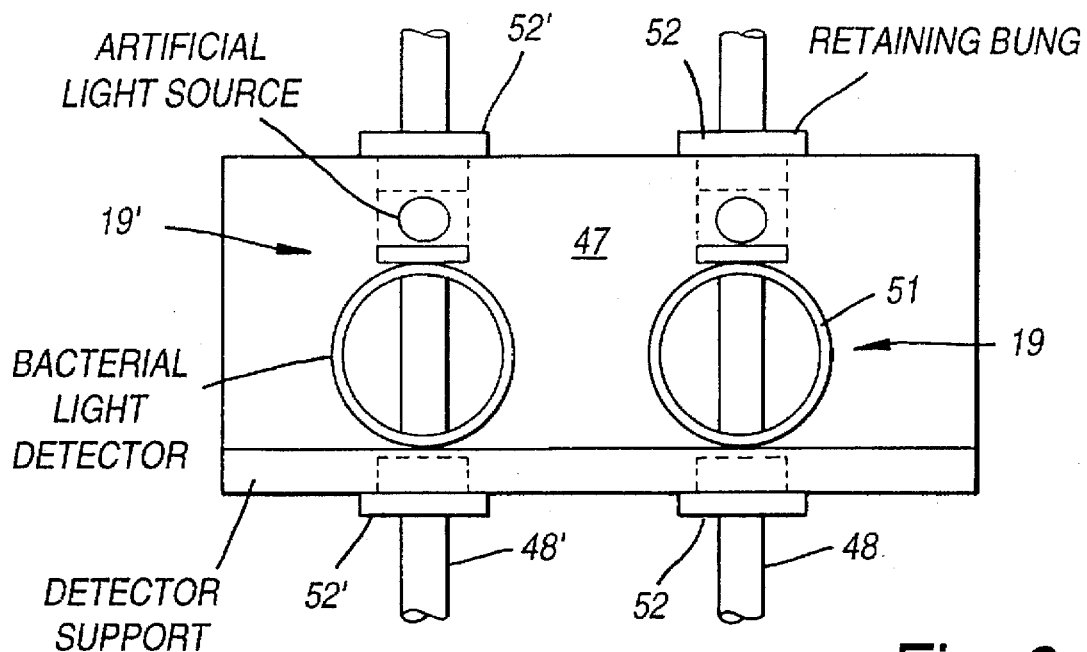
Figure 3B:
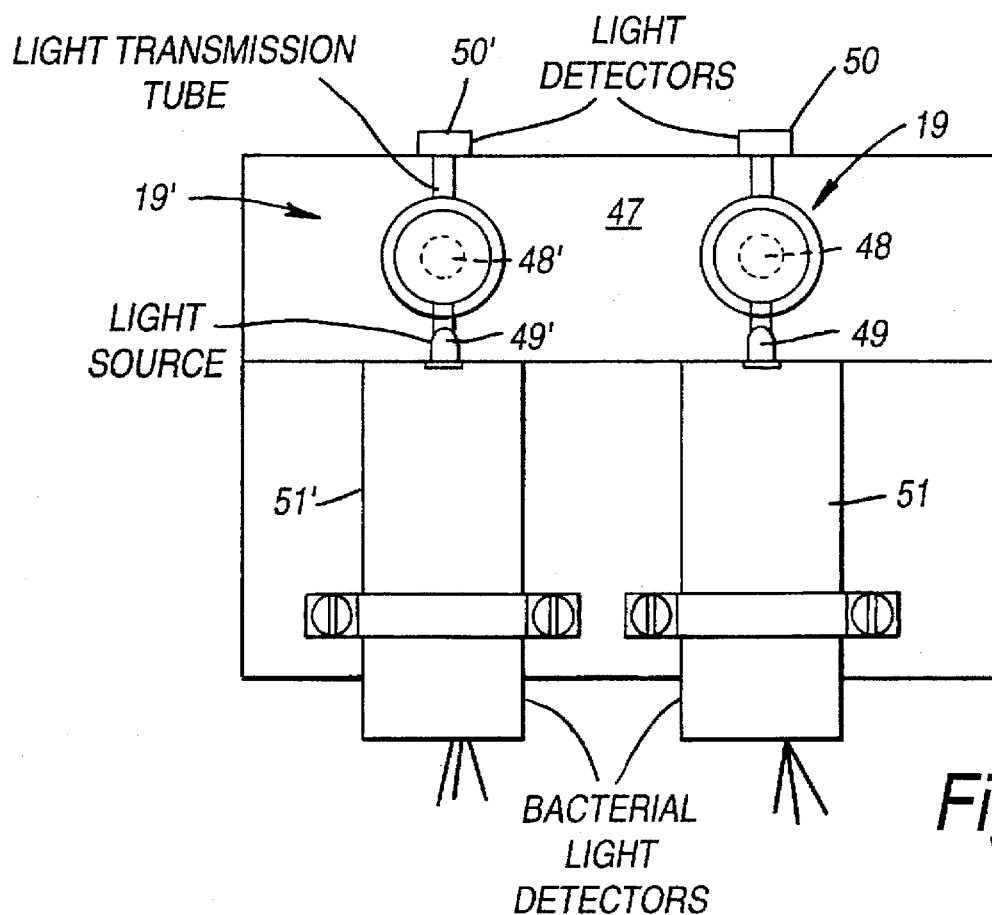

One embodiment of the invention will now be described by way of example only with reference to the accompanying drawings, in which, FIG. 1 is a generally schematic block diagram of aqueous sample toxicity measuring apparatus;

FIGS. 2a, 2b and 2c are somewhat schematic block diagrams of a reagent storage reservoir shown in FIG. 1 together with apparatus for filling the reservoir, and, FIGS. 3a and 3b are a front view and a top view respectively, showing in detail a flow cell detector block, parts of which are shown in FIG. 1.

Referring now to FIG. 1, an aqueous sample to be tested for toxicity is fed to apparatus shown within a broken line 1, via an aqueous sample inlet pipe 2. The inlet pipe 2 feeds an inlet port 3 of a three port valve 4, having outlet ports 5 and 6. The valve 4 can thus be set so that the inlet port 3 is connected either to the outlet port 5 or to the outlet port 6. When the inlet port 3 is connected to the outlet port 5, the aqueous sample travels via the inlet port 3 through the valve 4 to a pipe 7 which feeds a drain 8. The outlet port 6 is connected to an aqueous sample reservoir 9 and to a valve 10, which may be set in an open or alternatively in a closed state. Thus, when the inlet port 3 of the valve 4 is connected to the outlet port 6 and the valve 10 is closed, the aqueous sample is fed via the inlet port 3 of the valve 4 to fill the sample chamber 9. In order to control the level of aqueous sample in the sample chamber 9, a level sensing device 11 is provided, signals from the level sensing device 11 being used to control the valve 4 so that the sample chamber 9 is filled appropriately when required.

Aqueous samples from the sample reservoir 9 are fed via a valve 12 to a mixing chamber 13. The mixing chamber 13 is fed also via a valve 14 with diluent from a diluent reservoir 15, and via a valve 16 with a reagent from a reagent reservoir 17. The reagent reservoir 17 is stored within a reagent storage area which is enclosed by a broken line 18. Means to control the temperature of the measurement area within the broken line 1 and the reagent storage area within the broken line 18 are provided (not shown) so that the temperature within the measurement area is maintained between 15° and 30° C., whereas the reagent storage area is maintained at a temperature of 2° C. ±1° C.

The mixing chamber 13 is arranged to feed a detector cell 19, which detector cell 19 is coupled via a pipe 20 and valves 21 and 22 to a linear pump 23. The valve 21 is provided with ports 24, 25 and 26, wherein the ports 24 and 25 may be coupled or alternatively the ports 24 and 26 may be coupled. The valve 22 on the other hand is provided with ports 27, 28 and 29, wherein it can be arranged that either the ports 28 and 29 are coupled or the ports 27 and 29 are coupled. The port 25 of the valve 21 is coupled via a pipe 30 to communicate with an upper part 13a of the mixing chamber 13, whereas a lower part 13b of the mixing chamber 13 is arranged to be vented via a pipe 31 and a valve 32 to atmosphere.

In order to make a measurement of the toxicity of a aqueous sample, operation is as follows. Before a measurement is commenced, the ports 3 and 5 of the valve 4 may be assumed to be coupled so that aqueous sample liquid is fed to the drain 8 via the pipe 7, the sample reservoir 9 having been emptied through the drain 8 via the valve 10. At the start of a measurement the ports 3 and 6 of the valve 4 are coupled and the valve 10 is closed so that the aqueous sample liquid is fed via the valve 4 to fill the sample reservoir 9 to a level as determined by the level sensor 11. Assuming that the mixing chamber 13 is empty and that the diluent reservoir 15 and reagent reservoir 17 are primed with saline solution and reagent solution respectively, and that the valves 32, 14 and 16 are closed, the linear pump is placed in communication with the detector cell 19, via ports 29 and 27 of the valve 22 and ports 24 and 25 of the valve 21, and the valve 12 is opened. A predetermined volume of aqueous sample is then transferred from the sample reservoir 9 via the valve 12 to the mixing chamber 13 due to operation of the pump 23, by opening the valve 12 for a predetermined period. The valve 12 is then closed and the valves 14 and 16 are thereafter opened sequentially for predetermined periods, whereby a required volume of diluent and reagent respectively are transferred from the reservoirs 15 and 17 respectively to the mixing chamber due to continued operation of the linear pump 23. With the valves 12, 14 and 16 closed, valve 32 is opened to atmosphere. Then consequent upon continued operation of the linear pump 23, air is sucked from the upper part 13a of the mixing chamber 13, whereby atmospheric air is fed to the lower part 13b of the mixing chamber 13 via the pipe 31 to replace it. Air thus bubbles up within the mixing chamber 13 to effect thorough mixing of the aqueous sample, the diluent and the reagent within the mixing chamber 13.

After mixing, the valve 21 is operated so that the port 26 is coupled to the port 24 and consequent upon further operation of the linear pump 23, mixed constituents comprising the sample, the diluent and the reagent are drawn from the mixing chamber 13 through the detector cell 19. During a period when the detector cell 19 is filled with the mixture, a reading appertaining to toxicity is taken as will hereinafter be explained.

At completion of a measurement sequence, the linear pump 23 (which is a piston pump) is reversed so that the contents of its cylinder are expelled via the valve 22 to the drain 8. The valves 21, 22 and 32 are also appropriately operated to drain the mixing chamber in readiness for the next operation. Additionally, it will be appreciated that if required, diluent may be used to flush the mixing chamber prior to the next measurement and this may be achieved by appropriate operation of the valve 14 and the pump 23.

It will be appreciated that by using the linear pump 23, (which as already explained simply comprises a piston pump), on its suction stroke, appropriate proportions of aqueous sample, diluent and reagent can easily be transferred to the mixing chamber simply by opening the valves 12, 14 and 16 as appropriate for predetermined periods. Additionally, by using the pump to suck air through the mixture prior to making a measurement, thorough mixing of the constituents is guaranteed.

As shown in FIG. 1, the-measurement area 1 is divided into two parts, A and B, by a double broken line 1a. This division is for the purposes of explanation only and it should be understood that the apparatus shown in parts A and B are positioned along side each other within the measurement area. The apparatus thus far described is shown above the double broken line 1a in the part A and comprises apparatus for mixing in the mixing chamber 13 aqueous sample, diluent and reagent. However, in order to compensate for the colour and turbidity of the sample, and natural variations in bioluminescence, apparatus in the part B shown below the double broken line 1a is provided, comprising a mixing chamber 13' and a control detector cell 19' which is fed with diluent and reagent only from the reservoirs 15 and 17 respectively. Operation of the apparatus shown in the part B will not be described in detail since the manner of operation is substantially the same as corresponding apparatus in the part A, the various parts being distinguished only by a 'dash' suffix of corresponding reference numerals. Thus, the apparatus shown in the part B is operated using air for mixing the diluent and the reagent only in the mixing chamber 13' and using timed valve operation and the linear pump 23' to feed predetermined proportions of diluent and reagent to the mixing chamber 13'.

Operation of the valves and pumps shown in FIG. 1 is effected under control of a central processor unit (CPU) 43, control lines 44 being provided to communicate with the various valves and pumps. Signals from the sample detector cell 19 and control detector cell 19' are fed to the CPU via a line 45 and data output signals indicative of toxicity are provided on an output line 46.

Referring now to FIGS. 2a, 2b and 2c, the manner in which the reagent reservoir 17 is filled will now be described.

In the present example, the reagent contained in the reagent reservoir 17, comprises freeze-dried *Photobacterium phosphoreum* mixed with a predetermined volume of a reconstitution saline solution. As shown in FIGS. 2a, 2b and 2c, wherein parts corresponding to those in FIG. 1 bear the same numerical designations, freeze-dried bacteria is contained in a vial 33 under vacuum and reconstitution solution is contained in a vessel 34. The vial 33 is sealed by an elastic bung 35 and positioned beneath a pair of hollow needles 36 and 37, the hollow needle 36 being effectively longer than the hollow needle 37, whereby it projects further. The pair of needles are positioned side by side and operatively associated with apparatus 37a (shown schematically) which serves to raise or lower, as required, the pair of needles so that when required they can be lowered to pierce the bung successively, i.e. so that the hollow needle 36 penetrates the bung 35 to pass therethrough before the hollow needle 37. Prior to piercing of the bung 35, the apparatus is as shown in FIG. 2a with the vial 33 being positioned below the hollow needles 36, 37. In order to fill the reagent reservoir 17, the hollow needles 36, 37 are lowered as shown in FIG. 2b so that the hollow needle 36 only pierces the bung 35. As the hollow needle 36 pierces the bung 35, reconstitution solution is drawn via a pipe 38 and a pump 39, from the container 34 due to the vacuum within the vial 33. It will be appreciated that no pump action is required at this time, transfer of reconstitution solution from the container 34 to the vial 33 being effected solely due to the pressure differential therebetween. As the two hollow needles are lowered further, the hollow needle 37 pierces the bung 35, the pump 39 then being switched on so that reconstitution solution is pumped into the vial 33 via the pipe 38 to scour the vial of bacteria which is transferred with the reconstitution solution via a pipe 40 to the reagent reservoir 17. Although in the present example the pump 39 is coupled between the container 34 and the needle 36, in an alternative arrangement the pump 39 could be connected between the needle 37 and the reservoir 17. The reagent reservoir 17 is provided with a level sensor 41, signals from which are used to control operation of the pump 39 so that the reservoir 17 is filled to a predetermined level. As hereinbefore described with reference to FIG. 1, a predetermined volume of the reagent stored in the reservoir 17 is transferred when required via a pipe 42, which feeds the valve 16 and the mixing chamber 13.

It will be appreciated that by utilising a reagent reservoir which is filled as shown in FIG. 2a, FIG. 2b and FIG. 2c, with reconstituted bacteria, precise dilutions can be provided without the possibility of errors which might be introduced using manual procedures, and thorough mixing is effected. Typically, the bacteria are reconstituted into a 2% saline suspension.

The sample detector cell 19 and the control detector 19' shown in FIG. 1 are mounted together in a detector block 47 as shown in FIG. 3a and 3b. The sample detector 19 comprises a transparent tube 48 through which the mixture from the mixing chamber 13 passes. Light from a light source 49, which in this example is a light emitting diode, is arranged to pass through the tube 48 which contains the mixture, to a light detector 50. Thus, it will be appreciated that the output of the light detector 50 will be determined by the colour and/or turbidity of the sample in the tube 48. In order to detect light radiated by bioluminescence of bacteria in the mixture, a bioluminescence light detector 51 is provided. The control detector cell 19' is similarly constructed, comprising parts corresponding to those used in the sample detector cell 19 but distinguished by means of a 'dash' suffix. Signals from the various light detectors and signals for energising the light sources are provided as appropriate by the CPU 43. The sample detector cell 19 and the control detector cell 19' are supported in the detector block 47 by means of resilient retaining bungs 52, through which the transparent tubes 48 and 48' are arranged to pass.

In operation, aqueous sample, diluent and reagent is passed through the tube 48 of the sample detector cell 19, whereas reagent and diluent only are passed through the tube 48' of the control detector cell 19'. The detector block 47 serves several functions. It physically provides a mounting for the cells 19 and 19', the light sources 49 and 49' and the light detectors 50, 50', 51, 51', and it serves to shroud each of the light detectors from light produced in the other cell. It also provides a thermal mass which helps to damp any small fluctuations in the air temperature inside the measurement area. The wavelength of the light provided by the light sources is chosen to be close to the wavelength of light emitted by the bacteria and hence any sample constituents whose nature is to absorb or otherwise affect the light from the artificial light source will have a comparable effect on the light generated by the bacteria. By a comparison of the output of the two detector cells 19 and 19', at the commencement of each measurement, a colour/turbidity correction factor is calculated.

The amount of light output reduction due to a sample after the bacterial effects also seen in the control detector cell have been removed is directly in relation to the concentration of toxin present in the sample and is called Gamma (Γ). The basic calculation for Gamma (Γ), which is used as the indication of toxicity is as follows.

$$\Gamma = \left[ \frac{Ios}{Its} \times \frac{Itc}{Ioc} \right] - 1$$

Where:

'IOS' is the initial light output of the sample flow cell

'Its' is the light output of the sample flow cell at time t

'IOc' is the initial light output of the control flow cell

'Itc' is the light output of the control flow cell at time t.

The colour and turbidity correction is achieved by calculating what the value of Ios should be, based on the initial light seen in the sample detector cell 19, once the sample transmittance measured at the beginning of the toxicity measurement and any other offsets recorded have been taken into account. Any difference between the observed initial light and the calculated initial light is due to toxicity.

The equation used to calculate toxicity therefore becomes:

$$\Gamma \left[ \frac{Ioc \times Ktc \times C}{Its} \times \frac{Itc}{Ioc} \right] - 1$$

Where:

'Ktc' is the colour and turbidity correction factor, calculated from the output from the artificial light detectors:

$$Ktc = \left[ 1 - \frac{As}{2} \right] \times C$$

'As' is the sample absorption/transmittance factor. This is calculated from the output from the artificial light detectors when corrected for biofouling and offsets by comparison with the latest readings measured during a test performed whenever bacteria are reconstituted.

'C' is a correction factor for the offset between the initial light output from bacteria seen from the bacterial light detector once biofouling has been compensated for.

$$As = In\left[\frac{Vs}{Vc} \times \frac{Vcr}{Vsr}\right]$$

'Vs' is the output of the artificial light detector 50 of the sample detector cell 19 at the start of a measurement performed when the sample is present.

'Vc' is the output of the artificial light detector 50' of the control detector cell 19' when the sample is being measured.

'Vsr' is the output of the artificial light detector 50 of the sample detector cell 19 during test with diluent only.

'Vcr' is the output of the artificial light detector 50' of the control detector cell 19' during a test with diluent only.

The amount of light output reduction due to the sample, after the bacterial effects also seen in the control have been removed, is directly in relation to the concentration of toxin present in the sample and is called Gamma.

In operation of the apparatus, it is arranged for operation to be carried out in two basic modes, i.e. a learning mode and a monitoring mode. In the learning mode, the apparatus is arranged to monitor an aqueous sample by taking repeated measurements of the sample at three different concentrations of diluent and deriving a $EC_{50}$ concentration of the sample (i.e. a concentration extrapolated from three different measurements taken which would result in a 50% loss in the light output from the bacteria). The mean value of this $EC_{50}$ concentration is then used as the dilution of the sample in the monitoring mode. The monitoring mode comprises use of the apparatus to make repeated measurement of an aqueous sample at that one concentration and looks for fluctuations in the Gamma (Γ) figure measured. A Gamma (Γ) value, which exceeds the statistical norm derived in learning mode, causes the instrument to raise toxicity alarms and calculations to produce these figures are carried out in the CPU.

We claim:

1. Aqueous sample testing apparatus comprising a sample reservoir in which a sample to be tested is stored, a reagent reservoir, a diluent reservoir, a mixing chamber vented via a first valve to atmosphere through an air inlet tube which extends within the chamber towards a lower part thereof, second, third and fourth valves via which the sample, the reagent and the diluent respectively are fed selectively to the mixing chamber in accordance with the open/closed state of the said second, third or fourth valves, a detector cell fed with a mixture of the sample, the reagent and the diluent from the chamber, within which detector cell aqueous sample measurements are carried out, a linear pump and valve means, via which valve means the mixture is drawn through the detector cell from the chamber by the linear pump, or via which air in an upper part of the chamber is drawn from the chamber by the pump in accordance with the open/closed state of the said valve means, whereby for the purpose of mixing the sample, the reagent and the diluent, the said valve means is set so that air is drawn into the chamber via the inlet tube so as to bubble up through the mixture contained therein.

2. Apparatus as claimed in claim 1, comprising a central processor unit (CPU) used to control operation of the linear pump, the valves and the valve means in accordance with a predetermined programme.

3. Apparatus as claimed in claim 1, for the toxicity measurement of an aqueous sample, wherein the reagent comprises bioluminescent bacteria in an aqueous solution, the diluent comprises an aqueous solution, and the detector cell comprises light detector means arranged for detecting light given off by the bioluminescent bacteria in the mixture present in the said cell.

4. Apparatus as claimed in claim 3, wherein the proportion of diluent to sample is varied in dependence upon the toxicity of the sample as determined by the detector cell and for this purpose an appropriate signal is transmitted from the cell to the computer.

5. Apparatus as claimed in claim 4, wherein the proportion of diluent to sample is increased with toxicity of the sample.

6. Apparatus as claimed in claim 1, comprising further valve means via which sample in the sample reservoir is replaced for further measurements.

7. Apparatus as claimed in claim 1, wherein the diluent reservoir and the reagent reservoir is coupled via additional valve means, to an additional mixing chamber, which additional mixing chamber is coupled to an additional detector cell, a toxicity measurement appertaining to the sample being produced in dependence upon data derived both from the said detector cell and the said additional detector cell.

8. Apparatus as claimed in claim 7, wherein the said detector cell and the additional detector cell each comprise a light source operatively associated with a light detector positioned to receive light from the source after it has passed through the mixture in the cell with which it is associated and a bioluminescence detector for detecting light produced due to bacterial bioluminescence.

9. Apparatus as claimed in claim 1, comprising two compartments, the temperature of which are independently controllable, one of which compartments is used to accommodate the reagent reservoir and the other of which compartments is used to accommodate other parts of the apparatus including the sample reservoir, the diluent reservoir, the mixing chamber, the valves/valve means, the detector cell and the pump.

* * * * *